(12) United States Patent
Liu et al.

(10) Patent No.: US 11,612,415 B2
(45) Date of Patent: Mar. 28, 2023

(54) EXTERNAL LOCKING FIXATION DEVICE FOR EXTRA-ARTICULAR FRACTURES

(71) Applicant: The University of Toledo, Toledo, OH (US)

(72) Inventors: Jiayong Liu, Toledo, OH (US); Stephen J. Snider, Toledo, OH (US); David Dick, Toledo, OH (US); Vijay K. Goel, Toledo, OH (US); Nabil A. Ebraheim, Toledo, OH (US)

(73) Assignee: The University of Toledo, Toledo, OH (US)

(*) Notice: Subject to any disclaimer, the term of this patent is extended or adjusted under 35 U.S.C. 154(b) by 0 days.

(21) Appl. No.: 16/975,310

(22) PCT Filed: Feb. 26, 2019

(86) PCT No.: PCT/US2019/019516
§ 371 (c)(1),
(2) Date: Aug. 24, 2020

(87) PCT Pub. No.: WO2019/168815
PCT Pub. Date: Sep. 6, 2019

(65) Prior Publication Data
US 2020/0397482 A1     Dec. 24, 2020

Related U.S. Application Data

(60) Provisional application No. 62/635,678, filed on Feb. 27, 2018.

(51) Int. Cl.
*A61B 17/66* (2006.01)
*A61B 17/80* (2006.01)

(52) U.S. Cl.
CPC .......... *A61B 17/66* (2013.01); *A61B 17/8004* (2013.01)

(58) Field of Classification Search
CPC ..... A61B 17/66; A61B 17/8004; A61B 17/56; A61B 17/80
USPC .................................................... 606/53–59
See application file for complete search history.

(56) References Cited

U.S. PATENT DOCUMENTS

| | | | | |
|---|---|---|---|---|
| 2,371,519 A | * | 3/1945 | Haynes | A61B 17/6408 606/54 |
| 5,330,474 A | * | 7/1994 | Lin | A61B 17/7008 606/267 |
| 5,468,241 A | * | 11/1995 | Metz-Stavenhagen | A61B 17/6416 606/319 |
| 5,803,924 A | * | 9/1998 | Oni | A61B 17/6416 606/54 |
| 6,752,808 B2 | * | 6/2004 | Schumacher | A61B 17/663 606/90 |
| 10,159,511 B2 | * | 12/2018 | Lin | A61B 17/62 |
| 2006/0173462 A1 | * | 8/2006 | Kay | A61B 17/863 606/907 |

(Continued)

*Primary Examiner* — Eduardo C Robert
*Assistant Examiner* — Tara Rose E Carter
(74) *Attorney, Agent, or Firm* — MacMillan, Sobanski & Todd, LLC (57) ABSTRACT

A locking fixation device for treating extra-articular fractures includes a connector assembly connected to two end plates. Rotation of the connector assembly about an axis extending therethrough converts rotational motion to linear motion, and advances the end plates in a linear direction away from (lengthening) or toward (compression) each other.

22 Claims, 10 Drawing Sheets

(56) References Cited

U.S. PATENT DOCUMENTS

2017/0281235 A1* 10/2017 Lin ................. A61B 17/66

* cited by examiner

EXTERNAL LOCKING FIXATION DEVICE FOR EXTRA-ARTICULAR FRACTURES

CROSS-REFERENCE TO RELATED APPLICATIONS

This application claims the benefit of U.S. Provisional Application Ser. No. 62/635,678 filed Feb. 27, 2018, the entire disclosure of which is expressly incorporated herein by reference.

STATEMENT REGARDING FEDERALLY SPONSORED RESEARCH

The invention was not made with any U.S. Government support, and the United States Government has no rights in the invention.

BACKGROUND OF THE INVENTION

Extra-articular fractures are fractures that occur outside of a joint. For example, tibia fractures are generally classified by location as proximal tibia, diaphysis, and distal tibia fractures. Extra-articular tibia fractures include proximal tibia fractures without involving the knee joints, diaphysis fractures, and distal tibia fractures without involving the ankle joints. Such fractures are often associated with many serious complications and often result in long-term disability.

Current surgical treatment methods/devices include the use of an intramedullary rod, an internal locking or non-locking plate, and/or an external fixator. However, there are some significant drawbacks for these current surgical treatment methods/devices.

For example, the intramedullary rod device is a widely preferred procedure which allows for almost immediate weight bearing. However, insertion of an intramedullary rod is an invasive procedure which further compromises intramedullary blood supply. In addition, a second surgical procedure is often required for removal of the nail and/or screws, or to change the rod. Among potential complications are delayed union, nonunion, infection, deep vein thrombosis and/or pulmonary embolism.

The internal locking or non-locking plate device is used for far distal or far proximal or intra-articular tibia fracture fixation. This procedure is also invasive, and may further disrupt the pericortical bone blood perfusion. In addition, a second operation is required in up to 40% of patients.

The external fixator device is useful for temporary immobilization but is bulky and inconvenient for patients. A frequent complication is a biomechanically inappropriate fixation where one or more of the externally extending pins is easily pulled out.

There is a great need for improvements in treating such fractures. As such, orthopedists have recently resorted to using a femur-locking plate externally to treat tibia fractures in an off-label manner (See, for example, Kerkhoffs et al. JOT 2003; and, Kloen et al. JOT2008; Ma et al. Acta Orthop 2010; Zhang et al. JOT 2015; Ma et al. Injury 2017). Since these off-label locking plates were originally designed for femur internal fixation, the size and shape of the plate are not optimized for tibia fracture types and/or patients' needs.

In other situations, internally placed devices are also used in bone lengthening procedures which currently consists of surgical interventions similar to those used in fracture fixation.

Thus, there is a need for improvements in the field of orthopedics in the treatment of extra-articular fractures using a relatively minimally invasive approach and without the need for further major invasive procedures.

SUMMARY OF THE INVENTION

In one aspect, there is provided improvements in the field of orthopedics in the treatment of extra-articular fractures using a relatively minimally invasive approach and without the need for further major invasive procedures.

While the locking fixation device is described herein in connection with treatment of tibial fractures, it is to be understood, that in other circumstances, such device can be used to externally fixate other long bones, such as a fibula, femur, humerus, radius and ulna.

Described here is an external locking fixation device for treating an extra-articular fracture that includes a connector assembly, and first and second end plates. The first end plate and the second end plate are mounted on opposite ends of the connector assembly. Rotation of the connector assembly about an axis extending therethrough converts rotational motion to linear motion, and advances the proximal plate and the distal plate in a linear direction away from or toward each other.

The connector assembly has a threaded proximal end and a threaded distal end. The connector assembly is operatively connected at the proximal end to the proximal plate and operatively connected at the second end to the distal plate. The threaded proximal end and the proximal plate are threaded in a first direction, and the threaded distal end and the distal plate are in an opposite direction with respect to the threaded proximal end and proximal plate. In use, the rotation of the connector assembly about an axis extending therethrough converts rotational motion to linear motion, and advances the proximal plate and the distal plate in a linear direction away from each other.

In certain embodiment, the connector assembly has an internally threaded proximal end and an internally threaded distal end.

In other embodiments, the connector assembly has an externally threaded proximal end and an externally threaded distal end.

Also, in certain embodiments, one or more of the proximal and distal plates can also include one or more bars which define an opening configured for allowing for placement of one or more screws and a wide variety of angles appropriate to fracture anatomy.

In use, the locking fixation device is placed external to the skin (supradermal). The locking fixation device is adjustable so that the physician can accurately place the device upon initially setting the fracture. Also, the locking fixation device can be externally adjusted, if necessary to continue with alignment of the setting bones.

With the locking fixation device, there is no need for multiple rods with differing lengths present in the operating room in order to ensure proper matching with bone size. Also, there is no need for soft tissue dissection. The locking fixation device can be immediately used, without concern for the soft tissue swelling that occurs upon at the time of the break.

Basing on the different types of extra-articular fractures, the device can have different combinations, such as using a single plate alone (FIG. 4), or using a different proximal and distal plates (Please see the FIGS. 8-12).

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

DETAILED DESCRIPTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Figure 1:
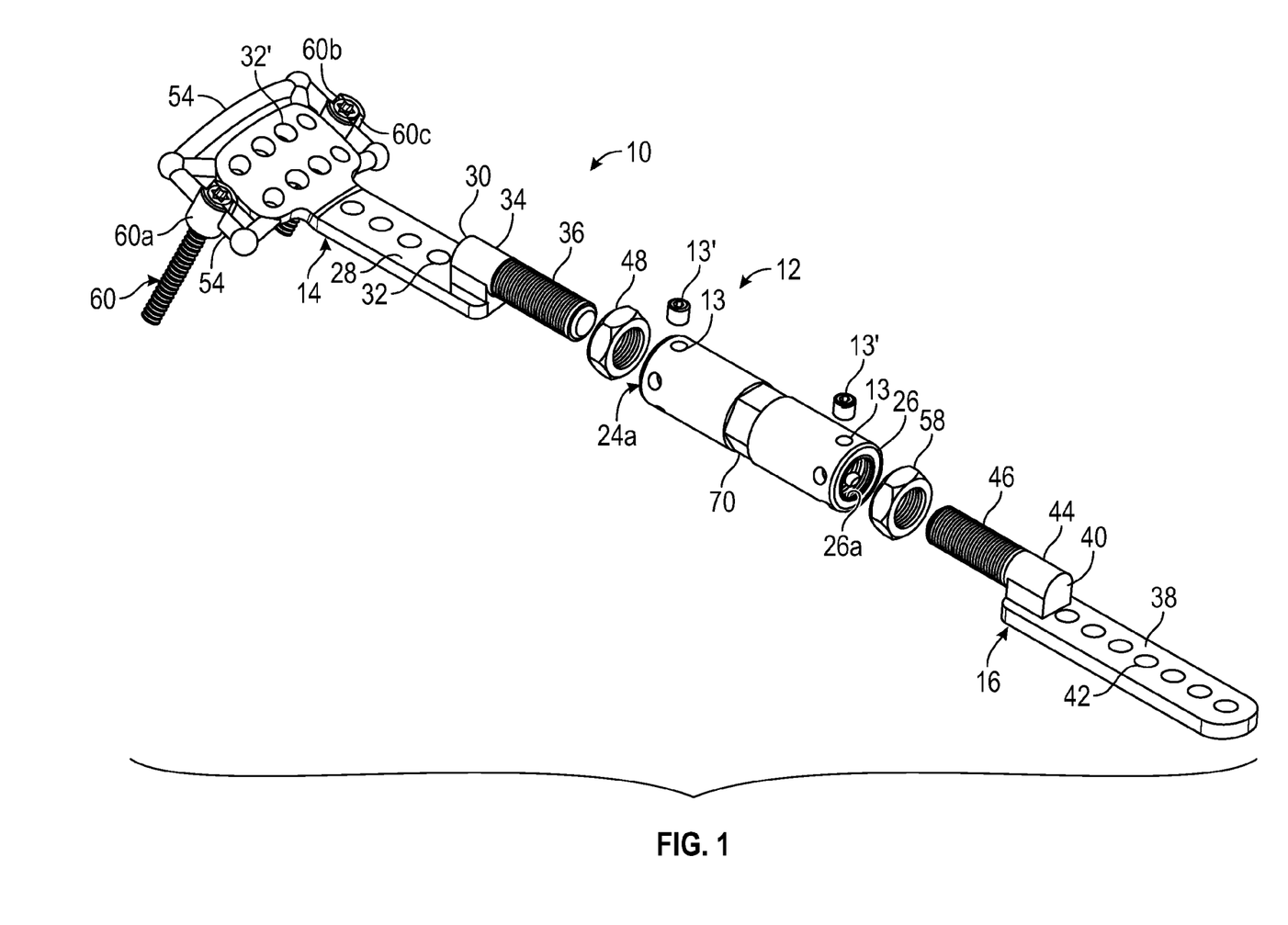
FIG. 1. Schematic exploded perspective view of one embodiment of a locking fixation device.
Figure 2:
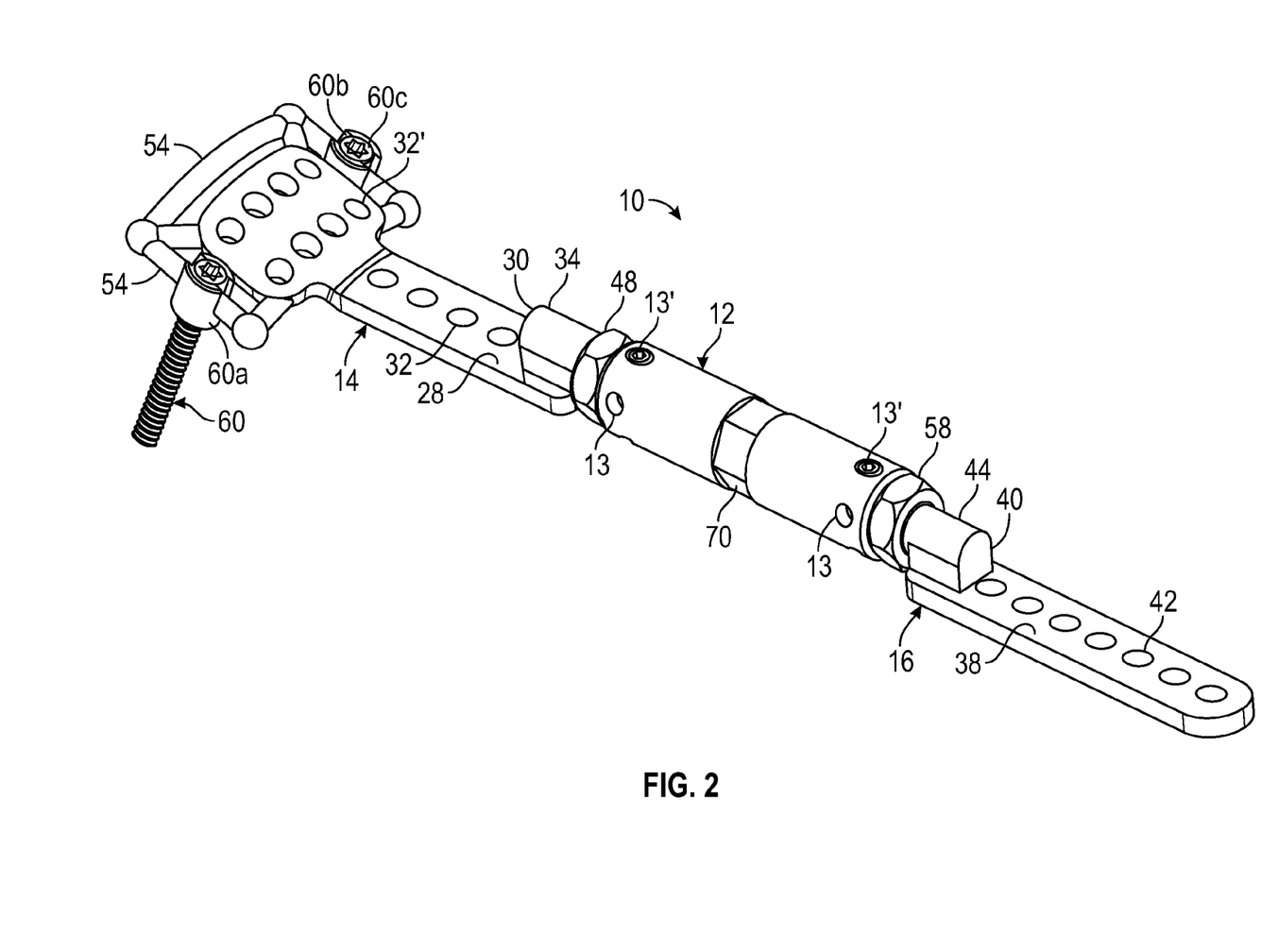
FIG. 2. Schematic perspective view of the embodiment shown in FIG. 1.

FIGS. 1-2 show one embodiment of a locking fixation device 10 having a central connector assembly 12, a first end plate 14, which can be used proximally or distally, and a second end plate 16, which also can be used proximally or distally.

The connector assembly 12 defines a longitudinally extending axis, and has a first end 24, which is adjacent to the first end plate 14, and second end 26, which is adjacent the second end plate 16. In the embodiment shown, the connector assembly 12 has a cylindrical cross-sectional area, but it is to be understood that in other embodiments, the outer surface can have other cross-sectional shapes, such as hexagonal, rectangular, square, and the like.

The connector assembly 12 has a threaded portion 24a that is at least partially hollow near the first end 24 and is internally threaded in a first direction. The second end 26 of the connector assembly 12 has a threaded portion 26a that is also partially hollow, and is internally threaded in an opposite direction to the threaded portion 24a of the first end 24.

The first end plate 14 has a screw receiving platform 28. In the embodiment in FIGS. 1-2, the first end plate 14 can have top surface 30 so that the first end plate 14 generally conforms to a patient's external lower extremity without touching the patient, thereby preventing skin and soft tissue ulcers or necrosis from undue pressure points.

A plurality of openings 32 extend through the screw receiving platform 28. One or more of the openings 32 can extend in a generally perpendicular direction with respect to a plane defined by the screw receiving platform 28, or can extend at an angle with respect thereto.

Figure 3:
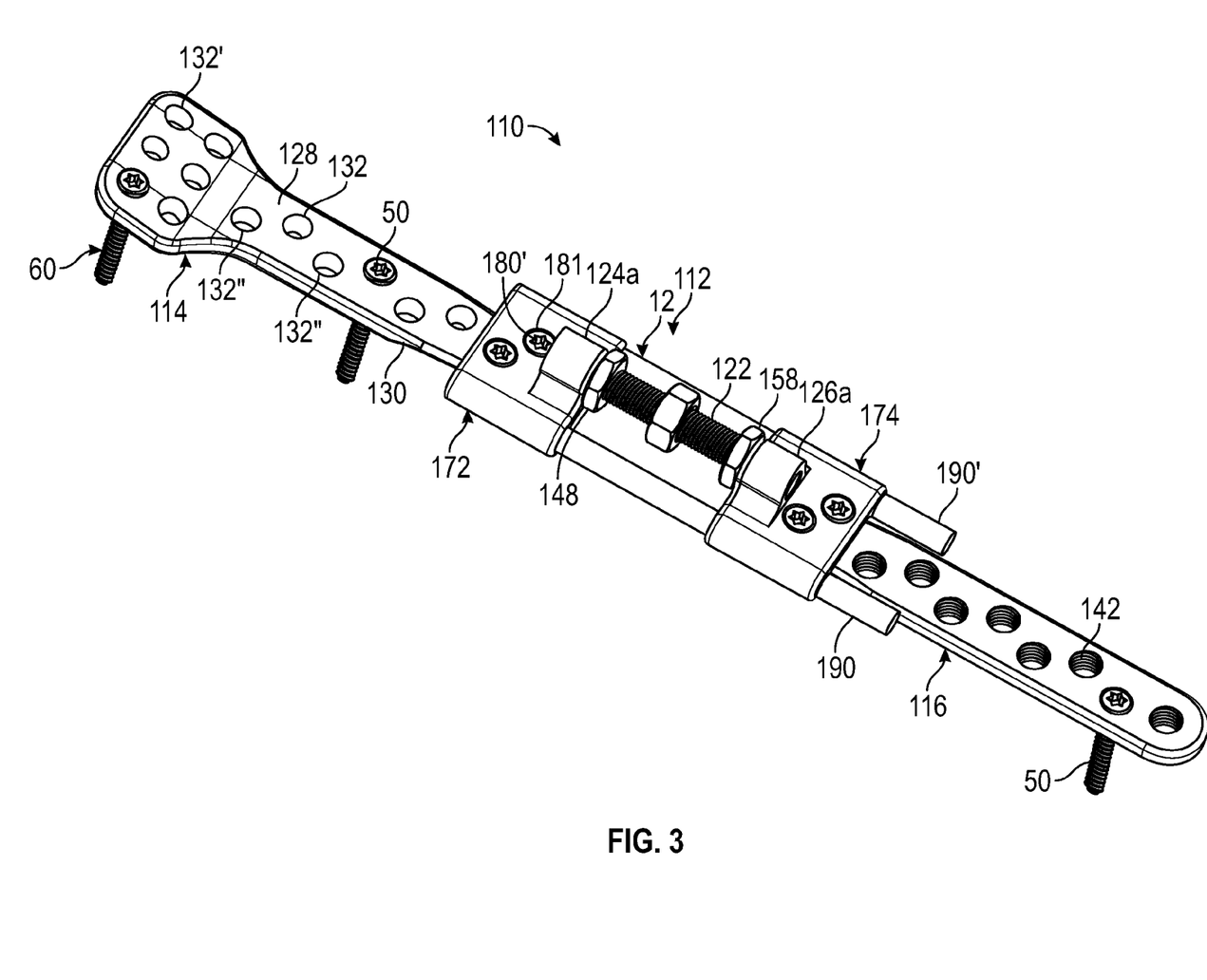
FIG. 3. Schematic perspective view of another embodiment of a locking fixation device.

In the embodiment shown in FIG. 1, the screw-receiving platform 28 can have the plurality of openings 32 that are generally in a series of rows (shown as 32') in order to allow a physician to determine which particular opening (and type of screw) would be best suited for fixation. The openings 32 can be in a particular pattern allowing for passage of locking-screws 50 (as shown in FIG. 3) at fixed or variable angles, which will pierce the skin and fix bone and bone fragments avoiding major neurovascular bundles and eliminating extensive tissue dissection.

Also, the plurality of openings 32 can extend along the first end plate 14 in a direction toward a neck portion 34 of the first end plate 14. It is to be understood that in other embodiments, the screw-receiving platform 28 can have other configurations of rows of openings 32. The variety of opening 32, 32' in a particular pattern allows for passage of locking-screws at fixed angles, which will pierce the skin and fix bone and bone fragments avoiding major neurovascular bundles and eliminating extensive tissue dissection.

The neck portion 34 extends in an angled direction from the angled surface 30 such that the neck portion 34 is resting comfortably on the external skin without causing undue pressure.

The neck portion 34 terminates at an externally threaded cylindrical portion 36. The threads of the threaded portion 36 are configured to engage in the threaded first end 24 of the connector assembly 12.

A first nut 48 can be positioned at the first end 24 of the connector assembly 12 and the threaded portion 36 to allow for a tightening once a desired fixation position has been determined. The connector assembly 12 can include radially extending holes 13 which are configured to allow the insertion of radially extending tightening screws 13' which secure the threaded portion 36 of the first end plate 14 and the connector assembly 12 in the desired fixation position.

In certain embodiments, the first end plate 14 can further include one or more bars 54 which extends outwardly from a far end of the screw-receiving platform 28. FIGS. 1-2 show the bar 54 hold the screw 60 which is configured to receiving a polyaxial cannulated screw 60. The bar 54 allows for placement of polyaxial cannulated screws 60 at a wide variety of angles appropriately adapted to the fracture anatomy.

In a configuration similar to the first end plate 14, the second end plate 16 has a screw receiving platform 38 which can have a top surface 40 that at least partially conforms to a patient's external leg. A plurality of openings 42 extend through the screw receiving platform 38. One or more of the openings 42 can extend in a generally perpendicular direction with respect to the screw receiving platform 38, or can extend at an angle with respect thereto.

The plurality of openings can extend along the second end plate 16 in a direction toward a neck portion 44. It is to be understood that in other embodiments, the screw-receiving platform 38 can have other configurations of rows of openings 42. The variety of openings 42 in a particular pattern allows for passage of locking-screws at fixed angles, which will pierce the skin and fix bone and bone fragments.

The neck portion 44 extends in a sloped from the surface 40 such that the neck portion 44 is in a somewhat spaced apart relationship to the patient's leg.

The neck portion 44 terminates at a cylindrical externally threaded portion 46. The threads of the threaded portion 46 are configured to engage in the threaded second end 26 of the connector assembly 12.

A second nut 58 can be positioned at the second end 26 of the connector assembly 12 and the threaded portion 46 to allow for a tightening once a desired fixation position has been determined. As noted above, the connector assembly 12 can include radially extending holes 13 which are configured to allow the insertion of radially extending tightening screws 13' which secure the threaded portion 46 of the second end plate 16 and the connector assembly 12 in the desired fixation position.

In certain embodiments, the locking fixation device 10 can include a central locking section 70 that can be radially fixed, using, for example a cotter pin (not shown) to ensure that the connector assembly does not rotate after the locking fixation device 10 is positioned on and secured to the patient.

FIGS. 3-6 show another embodiment of a locking fixation device 110 having a central connector assembly 112, a first end plate 114, and a second end plate 116. It is to be understood that while FIGS. 3-6 show a male connector, in other embodiments, the arrangements shown in FIGS. 3-6 can be assembled as in FIG. 1, with the female parts built as part of the plates instead of an attachment.

The first end plate 114 has a screw receiving platform 128. In the embodiment in FIGS. 3-6, the first end plate 114 can have bottom surface 130 that is at least partially curved so that the first end plate 114 generally conforms to a patient's external lower extremity without touching the skin, thereby reducing skin and soft tissue ulcers or necrosis from undue pressure points.

A plurality of openings 132 extend through the screw receiving platform 128. One or more of the openings 132 can extend in a generally perpendicular direction with respect to a plane defined by the surface 130, or can extend at an angle with respect to the curved surface 130.

The screw-receiving platform 128 can have the plurality of openings 132 that are generally in a series of rows (shown as 132') in order to allow a physician to determine which particular opening would be best suited for fixation. Also, a further plurality of openings 132" can extend along the first end plate 114 in a direction toward a neck portion 134 of the first end plate 114. It is to be understood that in other embodiments, the screw-receiving platform 128 can have other configurations of rows of openings 132. The variety of opening 132, 132', 132" in a particular pattern allows for passage of locking-screws 50 at fixed or variable angles, which will pierce the skin and fix bone and bone fragments avoiding major neurovascular bundles and eliminating extensive tissue dissection.

The neck portion 134 extends in an angled direction from the surface 130 such that the neck portion 134 is resting comfortably on the external skin without causing undue pressure.

In a configuration similar to the first end plate 114, the second end plate 116 has a screw receiving platform 138 which can have a bottom surface 140 that at least partially conforms to a patient's external leg. A plurality of openings 142 extend through the screw receiving platform 138. One or more of the openings 142 can extend in a generally perpendicular direction with respect to the surface 140, or can extend at an angle with respect to the curved surface 140.

The screw-receiving platform 138 can have a plurality of openings 142 that are generally in a series of rows in order to allow physician to determine which particular opening would be best suited for fixation. Also, the plurality of openings 142 can extend along the second end plate 116 in a direction toward a neck portion 144. It is to be understood that in other embodiments, the screw-receiving platform 138 can have other configurations of rows of openings 142. The variety of openings 142, 142' in a particular pattern allows for passage of locking-screws 150 at fixed angles, which will pierce the skin and fix bone and bone fragments.

The neck portion 144 is shaped to conform to the opening 177 in the connector module 174 in order to provide a rigid connection when joined.

Referring in particular to FIG. 3, the connector assembly 112 includes a connecting rod 122, a first connector module 172, and a second connector module 174.

The connecting rod 122 defines a longitudinally extending axis, and has a first end 124, which is adjacent to the first end plate 114, and a second end 126, which is adjacent the second end plate 116.

The first end 124 of the connector rod 122 is threadably connected to a threaded portion 124a of the first connector module 172, while the second end 126 of the connector rod 122 is threadably connected to a threaded portion 126a of the second connector module 174. The first end 124 of connector rod 122 is threaded in a first direction. The second end 126 of the connector rod 113 is threaded in the opposite direction as the first end 124.

In the embodiment shown in FIGS. 3-6, the connector rod 122 includes a co-axial central driving member 180, such as a hexagonal nut. It is to be understood, however, that in other embodiments, the outer surface of the driving feature 180 can have other cross sectional shapes, such as rectangular, square, circular with holes, and the like.

The threaded portions 124a, 126a of the connector modules 172, 174 co-axially aligned with the axis defined by the connector rod 122. When the connecting rod 122 is rotated, the connector modules 172, 174 are moved either towards or away from each other, depending on the direction of rotation of the connecting rod 122.

Figure 5:
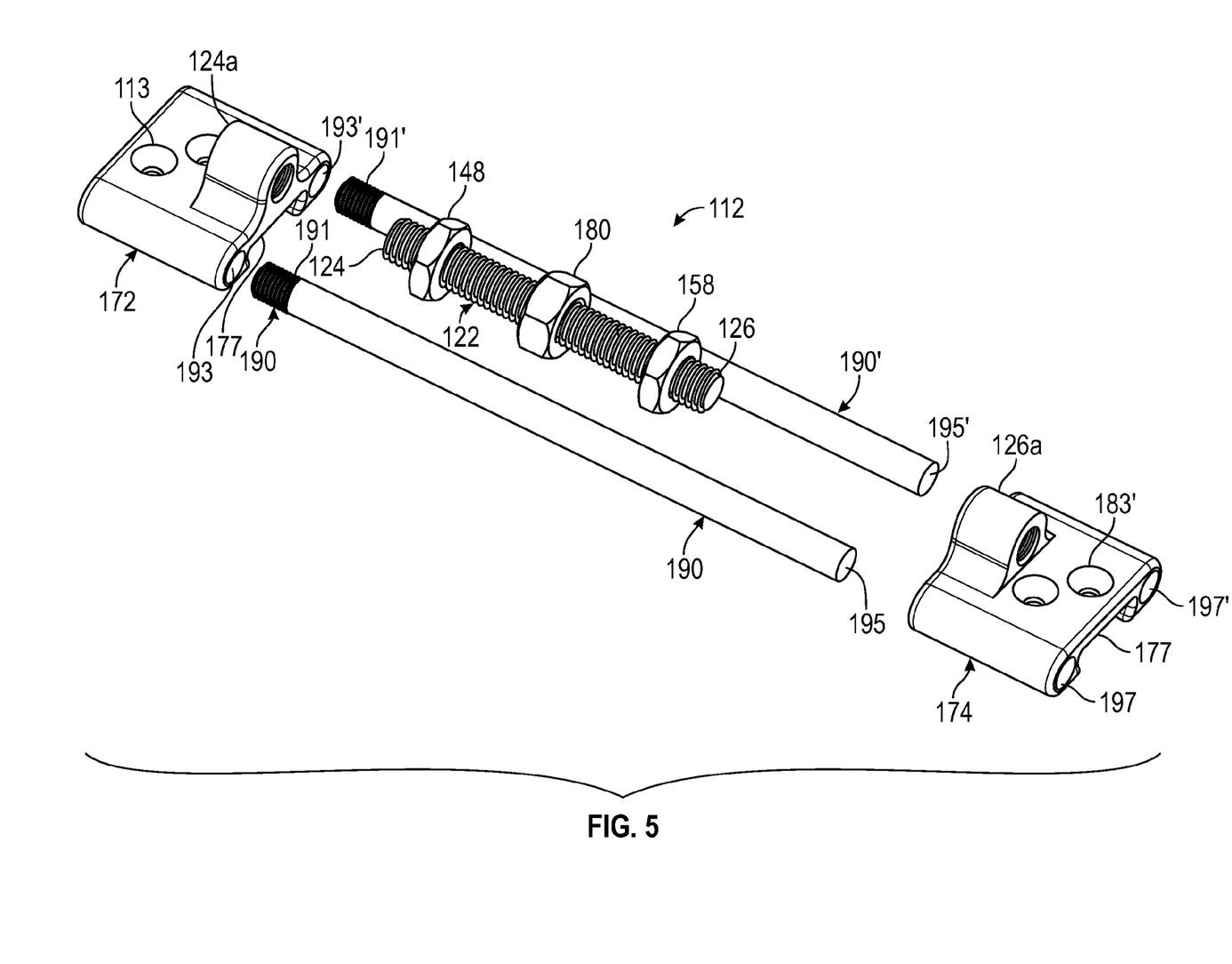
FIG. 5. Exploded perspective view of a connector assembly of a locking fixation device.

In the embodiment shown in FIGS. 3 and 5, one or both of the ends 124, 126 of the connecting rod 122 are provided with locking nuts 148, 158 with threads matching the direction of the corresponding ends of the connecting rod 122. When the connecting rod 122 has been rotated to achieve the desired degree of compression or distraction, the locking nuts 148, 158 are tightened against the connector modules 172, 174 to prevent further rotation. It is to be understood, that in other embodiments, this tightening function could be accomplished with other means, such as one or more set screws mounted on the connector modules. With multiple set screws and multiple longitudinal grooves in the threads of the connector rods, the connector rod could be locked in small, discrete increments.

Figure 6:
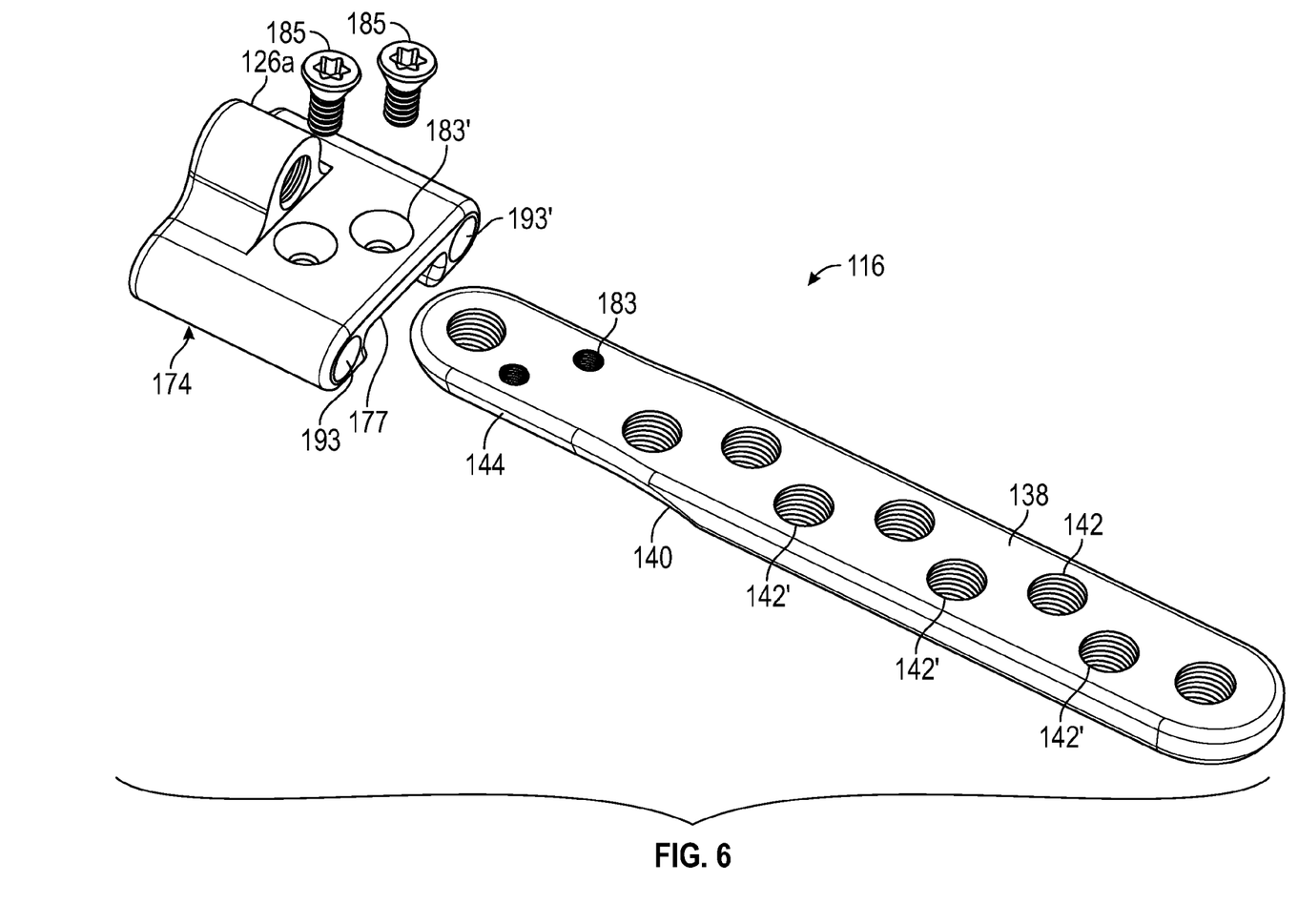
FIG. 6. Exploded perspective view of the connection between a plate and connector module of a locking fixation device.

The first module 172 defines an axially extending slot 175 that is configured to accept the neck portion 134 of the first end plate 114. That is, the neck portion 134 slidably engages/ dovetails into and can be axially moved along the slot 175. The first end plate 114 can be provided with one or more holes 180 that align with holes 180' that extend through the first connector module 172 to receive one or more screws 181. Similarly, the second module 174 defines an axially extending slot 177 that is configured to accept the neck portion 144 of the second end plate 116. That is, the neck portion 144 slidably engages/dovetails into and can be axially moved along the slot 177. The second end plate 116 can be provided with one or more holes 183 that align with holes 183' that extend through the second connector module 174 to receive one or more screws 181.

Although a dovetail is shown, other shapes could be used, as well as other fastening schemes, so long as clearance is maintained for the travel of the connector rod 122 above and for the patient's skin below.

Also, in certain embodiments, the connector assembly 112 can include one or more stabilizing rods 190, 190' to provide an anti-torque feature to prevent relative rotation of the two end plates 114, 116 while tightening the connecting device. The stabilizing rods 190,190' can have first threaded ends 191, 191' which threadably engage axially extending openings 193, 193' in the first module 172. The stabilizing rods 190, 190' can have opposing second ends 195, 195' which slidably engage axially extending openings 197, 197' in the second module 174.

Figure 4:
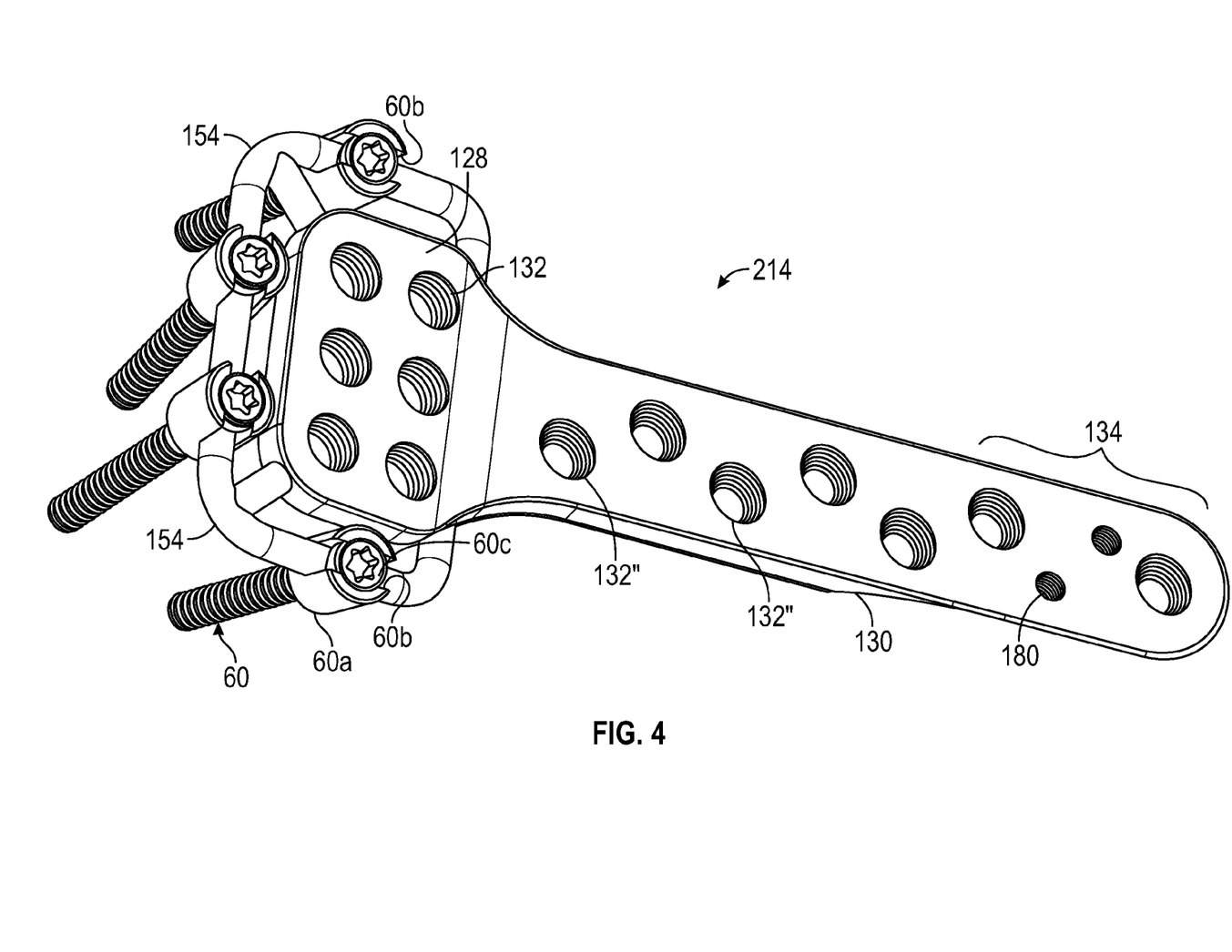
FIG. 4. Schematic perspective view of a proximal plate with side bar of a locking fixation device.

FIG. 4 shows another embodiment of a first end first end plate 214. For ease of explanation and comparison to FIG. 3, where the same features are shown, the same reference numbers are shown. Thus, the first end plate 214 has a screw receiving platform 128, a bottom surface 130, a plurality of openings 132, and a neck portion 134. Here, the first end plate 214 can further include one or more bars 154 which extends outwardly from a far end of the screw-receiving platform 128. The bar 154 allows for placement of polyaxial cannulated screws 60 at a wide variety of angles appropriately adapted to the fracture anatomy. In certain embodiments, as best shown in FIG. 4, the pedicle screw 60 has a cylinder 60a has a U-shaped notch 60b that acts as screw head. In the case of a variable screw, the U-shaped notch 60b engages the screw with a ball and socket type joint. The bar 154 lays in the U-shaped notch 60b, and the screw 60 is locked therein a set screw 60c. In use, when tightening the set screw, friction locks the ball and socket in place as well, fixing the angle of the screw.

Figure 7:
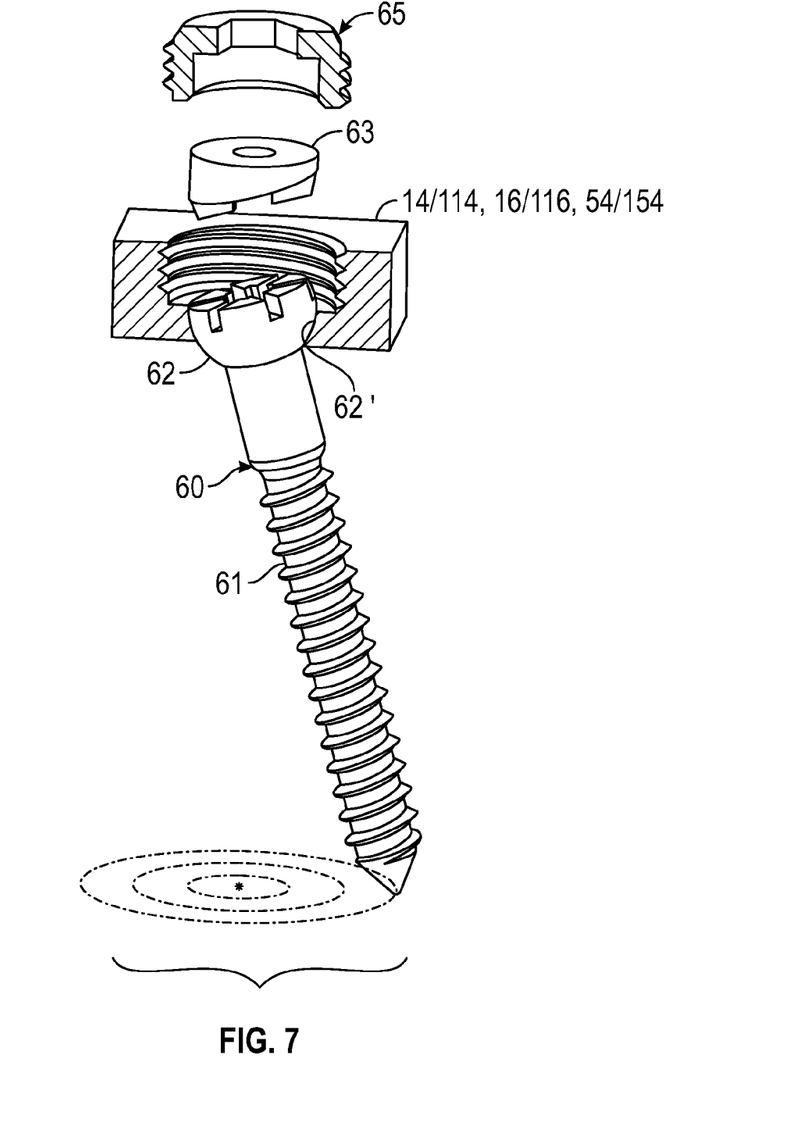
FIG. 7. Exploded perspective view, partially broken away, of an unassembled polyaxial variable angle screw having a hemispherical, flat-topped, slotted head in a portion of a locking fixation device; a wedge and a cap (broken away) useful with the polyaxial variable angle screw.
Figure 8:
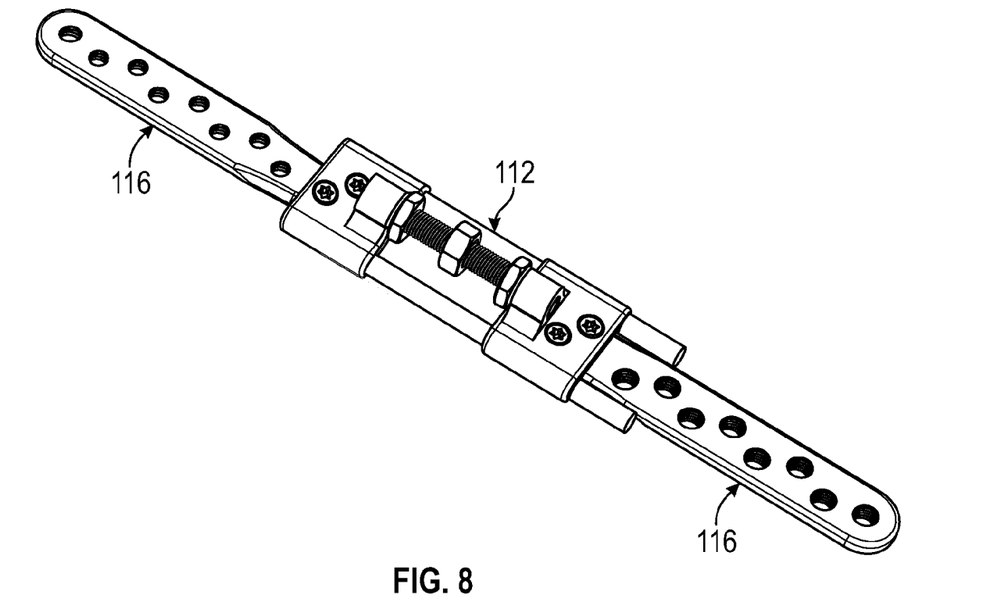
FIG. 8. Schematic perspective view showing one combination of the tibia plates. This combination is good for tibia diaphysis fractures.
Figure 9:
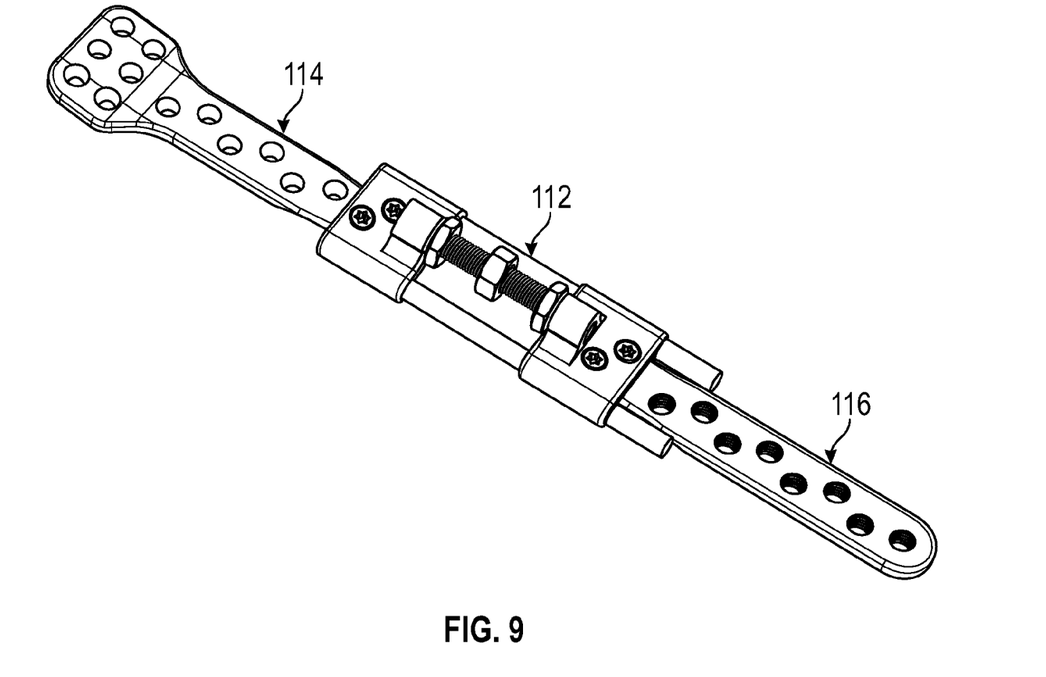
FIG. 9. Schematic perspective view showing another combination of the tibia plates. This combination is good for the tibia fractures located to either proximal or distal tibia.
Figure 10:
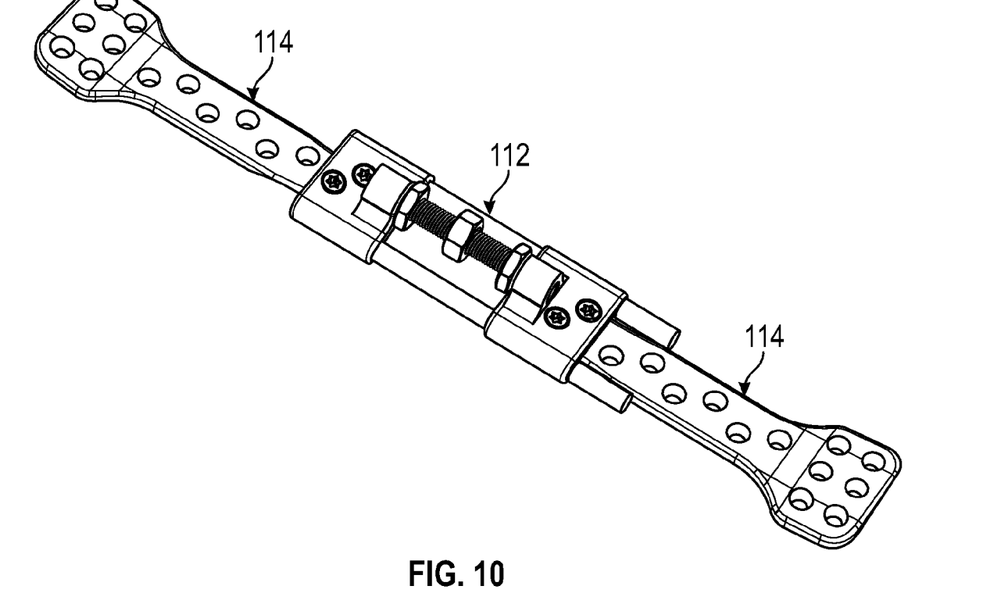
FIG. 10. Schematic perspective view showing another combination of the tibia plates. This combination is good for the fractures involved in both proximal and distal tibia.
Figure 11:
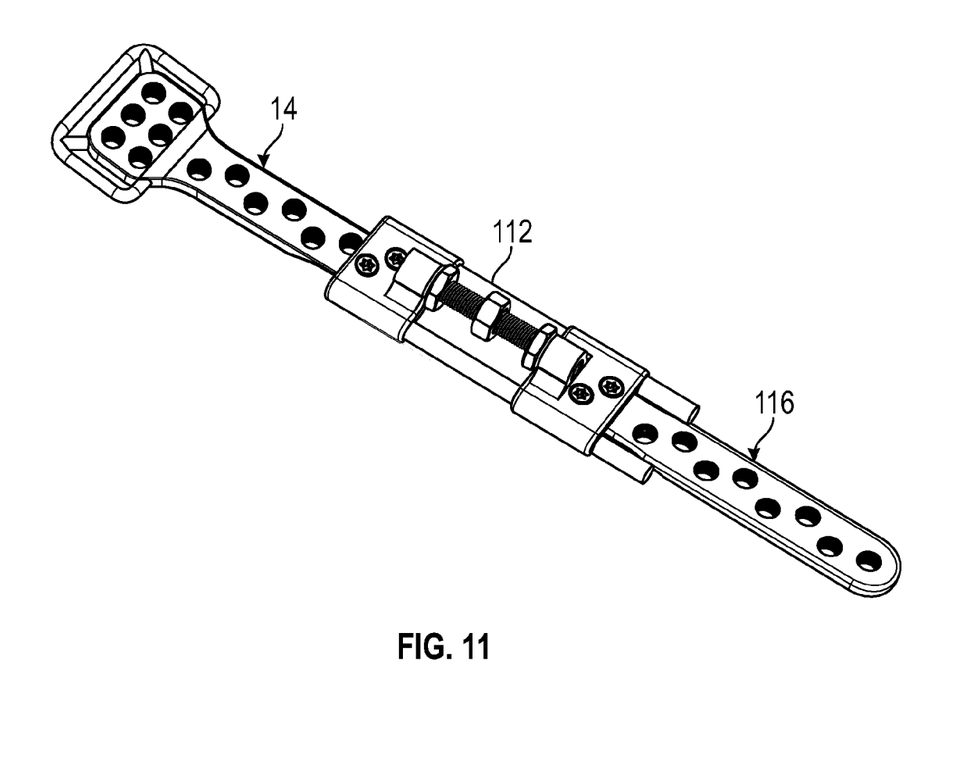
FIG. 11. Schematic perspective view showing another combination of the tibia plates. This combination is good for the tibia fractures located to either proximal or distal tibia, and the proximal or distal tibia fractures are comminuted. It potentially needs added more polyaxial screws for fixations.
Figure 12:
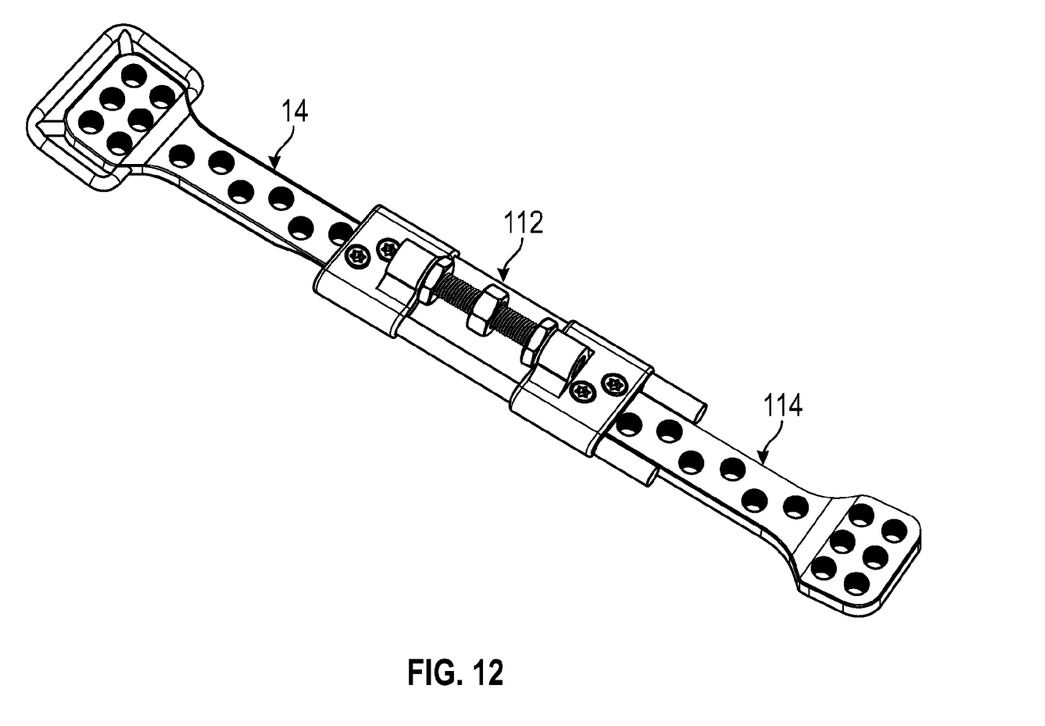
FIG. 12. Schematic perspective view showing another combination of the tibia plates. This combination is good for the fractures involved in both proximal and distal tibia. One end is comminuted and another end is not.

Referring now to FIG. 7, one embodiment of a suitable polyaxial cannulated screw 60 having a threaded shank 61 and a head 62 is shown. A spherical underside of the head 62 fits in a spherical bottom of a desired screw hole 62' in the first end plate 14/114, the second end plate 16/116 and/or a bar 54/154. The screw 60 is driven at a desired angle using a drill guide. A wedge 63, keyed to the screw head 62 and matching the driven angle of the screw, is placed on the screw head 62. The wedge 63 is tapered so as to present a top surface that is parallel to the proximal screw receiving platform 28/128, the distal screw receiving platform, 38/138 and/or a top surface of bars 54/154. A cap 65 is screwed onto or over the wedge 63, fixing the screw 60.

With such configuration, the radial direction of the screw is infinitely variable. Each desired angle from the vertical is set using the wedge and a drill guide. For example, one reasonable set would be 0°, 5°, 10°, and perhaps 15°.

FIGS. 8-12 provide schematic perspective views showing non-limiting examples of different combinations of the tibia plates. The FIG. 8 combination is good for tibia diaphysis fractures. The FIG. 9 combination is good for the tibia fractures located in either proximal or the distal tibia. The FIG. 10 combination is good for fractures involved in both proximal and distal tibia. The FIG. 11 combination is good for comminuted tibia fractures located at either the proximal or distal tibia. The FIG. 12 combination is good for the fractures involved in both proximal and distal tibia, where one end is comminuted and another end is not.

Examples of Tibia Fractures

The locking fixation device is an adjustable device size that allows for a 'universal' tibial fracture device. Use of the locking fixation device significantly lower revision rates and provides better fracture union rates.

Table 1 below show results of healing times and complications of patients with extra articular distal tibia fractures treated with external locking plate versus intramedullary rods.

| Device | Number of Patients | Healing time (weeks) | Complications |
| --- | --- | --- | --- |
| External locking plate fixation | 28 | 15.1 (9-22) | 0 |
| Intramedullary Rods | 30 | 17.8 (12-26) | Non-unions: 5 Delayed union: 2 Infection: 1 |

Then the locking fixation device is in use, the length and angles between the proximal plate and the distal plate may be adjusted by turning the connector assembly in a 'screw-like' manner, thus allowing for lengthening and/or compression of the limb as needed.

The locking fixation device provides for a better biological environment for fracture healing, as the proximal/distal plates are placed less invasively as only incisions for the screws must be made in the patient. Another benefit is the easy removal of the device in an outpatient setting that does not require a second major procedure as there are no internal plates.

The locking fixation device does not disrupt the underlying cortical bone perfusion, and decreases incidence of inflammatory complications from loosening of hardware.

The locking fixation device also provides for a better biomechanical environment for fracture healing, as the proximal/distal plates and resulting screw placement do not require precise adaptation of the proximal/distal plates to the underlying bone. This feature makes it impossible for the screw insertion to alter the reduction. Further, each screw plays an equal role in fixation, which reduces the changes for screws from pulling out or breaking as the screws are unlikely to loosen from the plate.

The external fixation devices are designed to sit above the skin, further from the bone than a conventional locking plate. As such, the external fixation devices are especially useful with variable angle screws that allow for better hit (or avoid) fracture lines, joint surfaces, and the like.

Also, the low-profile nature of the device provides a convenience to the patient and allows the device to be concealable under clothing.

Also, in certain uses, based on a clinical detailed situation, e.g., different fracture types and locations, the proximal plate and/or the distal plates can replace each other.

In still other uses, the proximal/distal plates can each be used alone when appropriate, as shown in FIG. 4. For example, in cases where both a distal and proximal plate are not needed, (e.g., where a fracture is very near either end of the tibia), the connector assembly may not be needed.

Because of this, the connector assembly otherwise incorporated on the plates may consist of a separate part that can be removably attached to the plates for use only when needed.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A locking fixation device for treating extra-articular fractures or for performing bone lengthening surgeries, comprising:
   a first end plate comprising a screw receiving platform through which a plurality of openings extend;
   a second end plate; and,
   a connector assembly having two threaded ends;
   one threaded end of the connector assembly being operatively connected to the first end plate, and the other threaded end of the connector assembly being operatively connected to the second end plate;
   the one threaded end and the second end plate being threaded in a first direction, and the other threaded end and the second end plate being threaded in an opposite direction;
   the connector assembly being configured to be rotatable about an axis extending therethrough, and configured to convert rotational motion to linear motion, thereby advancing the first and second end plates in a linear direction towards or away from each other achieving compression or lengthening functions, respectively;
   wherein the first end plate further comprises bars which extend outwardly from, and along a portion of a perimeter of, the screw receiving platform, wherein the bars include a screw hole having a spherical bottom.

2. The device of claim 1, wherein the two threaded ends are externally threaded.

3. The device of claim 2, wherein the connector assembly includes a connecting rod operatively connected at opposing ends to first and second connector modules;
   the connecting rod defining a longitudinally extending axis having a first end configured to threadably engage the first connector module, and a second end configured to engage the second connector module.

4. The device of claim 3, wherein one end of the connecting rod is threadably connected in a first direction to a threaded portion of the adjacent one of the first and second connector modules, and another end of the connecting rod is threadably connected in an opposing direction to a threaded portion of the other of the first and second connector modules.

5. The device of claim 2, wherein the connector assembly includes a co-axial central driving member, configured to rotate a connecting rod, whereby, when the connecting rod is rotated, first and second connector modules are configured to be moved either towards or away from each other, depending on the direction of rotation of the connecting rod.

6. The device of claim 2, wherein one of first and second connector modules defines an axially extending slot that is configured to accept a neck portion of one of the first and second end plates; and
   wherein the other of the first and second connector modules defines an axially extending slot that is configured to accept a neck portion of the other of the first and second end plates.

7. The device of claim 2, wherein one of the first and second end plates includes one or more radially extending holes that align with corresponding holes that extend through an adjacent one of first and second connector modules, wherein the aligned holes are configured to receive a screw; and
   wherein the other of the first and second end plates includes one or more radially extending holes that align with corresponding holes that extend through an adjacent other of the first and second connector modules, wherein the aligned holes are configured to receive a screw.

8. The device of claim 2, wherein the connector assembly further includes one or more stabilizing rods configured to provide an anti-torque feature to prevent relative rotation of the first and second end plates while tightening the connector assembly.

9. The device of claim 2, further comprising first and second connector modules, wherein the first connector module is integrally formed with the first end plate, and the second connector module is integrally formed with the second end plate.

10. The device of claim 1, wherein the screw receiving platform has a planar surface through which the plurality of threaded openings extend, the threaded openings each being configured to receive a polyaxial cannulated screw or a fixed locking screw; and
    wherein the second end plate has a distal screw receiving platform having a planar surface through which a plurality of distal threaded openings extend, each of the distal threaded openings being configured to receive a polyaxial cannulated screw or a fixed locking screw.

11. The device of claim 10, wherein the one or more of the threaded openings extend in a generally perpendicular direction with respect to the screw-receiving platform, or wherein one or more of the distal threaded openings extend at an angle with respect to the distal screw-receiving platform.

12. The device of claim 10, wherein the plurality of openings comprises a series of rows.

13. The device of claim 10, wherein the screw receiving platform has a bottom surface that is at least partially curved so that the first end plate is adapted to generally conform to a patient's external lower extremity without touching the patient.

14. A locking fixation device for treating extra-articular fractures or for performing bone lengthening surgeries, comprising:
    a first end plate comprising a screw receiving platform through which a plurality of openings extend;
    a second end plate; and,
    a connector assembly having two threaded ends;
    one threaded end of the connector assembly being operatively connected to the first end plate, and the other threaded end of the connector assembly being operatively connected to the second end plate;

the one threaded end and the second end plate being threaded in a first direction, and the other threaded end and the second end plate being threaded in an opposite direction;

the connector assembly being configured to be rotatable about an axis extending therethrough, and configured to convert rotational motion to linear motion, thereby advancing the first and second end plates in a linear direction towards or away from each other achieving compression or lengthening functions, respectively;

wherein the first end plate further comprises bars which extend outwardly from the screw receiving platform, wherein the bars include a screw hole having a spherical bottom; and wherein the two threaded ends of the connector assembly are internally threaded.

15. The device of claim 14, wherein the connector assembly is at least partially hollow near the one threaded end and is internally threaded in a first direction; and, wherein the connector assembly is at least partially hollow near the other threaded end and is internally threaded in the opposite direction.

16. The device of claim 14, wherein the first end plate includes a neck portion that extends in an angled direction from a surface of the screw receiving platform; or, wherein the second end plate includes a neck portion that extends from a surface of a distal screw receiving platform.

17. The device of claim 16, wherein the neck portion of the first end plate terminates at an externally threaded cylindrical portion, and is configured to engage one of the internally threaded ends of the connector assembly; or, wherein the neck portion of the second end plate terminates at an externally threaded cylindrical portion, and is configured to engage one of the internally threaded ends of the connector assembly.

18. The device of claim 14, wherein the connector assembly includes a central locking nut configured to be radially fixed to ensure that the connector assembly does not rotate after the locking fixation device is positioned on and secured to the patient.

19. The device of claim 14, wherein the connector assembly further includes at least one nut positioned at either of the two threaded ends of the connector assembly to allow for a tightening once a desired fixation position has been determined.

20. A locking fixation device for treating extra-articular fractures or for performing bone lengthening surgeries, comprising:

a first end plate comprising a screw receiving platform through which a plurality of openings extend;

a second end plate; and, a connector assembly having two threaded ends;

one threaded end of the connector assembly being operatively connected to the first end plate, and the other threaded end of the connector assembly being operatively connected to the second end plate;

the one threaded end and the second end plate being threaded in a first direction, and the other threaded end and the second end plate being threaded in an opposite direction;

the connector assembly being configured to be rotatable about an axis extending therethrough, and configured to convert rotational motion to linear motion, thereby advancing the first and second end plates in a linear direction towards or away from each other achieving compression or lengthening functions, respectively;

wherein the first end plate further comprises bars which extend outwardly from the screw receiving platform, wherein the bars include a screw hole having a spherical bottom;

wherein the two threaded ends are externally threaded; and wherein the connector assembly includes one or more locking nuts with threads matching the direction of the corresponding ends of connecting rods, whereby, when the connecting rods have been rotated to achieve the desired degree of compression or distraction, the locking nuts are configured to be tightened against first and/or second connector modules to prevent further rotation.

21. A locking fixation device for treating extra-articular fractures or for performing bone lengthening surgeries, comprising:

a first end plate comprising a screw receiving platform through which a plurality of openings extend;

a second end plate; and, a connector assembly having two threaded ends;

one threaded end of the connector assembly being operatively connected to the first end plate, and the other threaded end of the connector assembly being operatively connected to the second end plate;

the one threaded end and the second end plate being threaded in a first direction, and the other threaded end and the second end plate being threaded in an opposite direction;

the connector assembly being configured to be rotatable about an axis extending therethrough, and configured to convert rotational motion to linear motion, thereby advancing the first and second end plates in a linear direction towards or away from each other achieving compression or lengthening functions, respectively;

wherein the first end plate further comprises bars which extend outwardly from the screw receiving platform, wherein the bars include a screw hole having a spherical bottom;

wherein the two threaded ends are externally threaded;

wherein the connector assembly further includes one or more stabilizing rods configured to provide an anti-torque feature to prevent relative rotation of the first and second end plates while tightening the connector assembly; and wherein the stabilizing rods have first threaded ends which threadably engage axially extending openings in one of first and second connector modules; and, wherein the stabilizing rods have opposing second ends which slidably engage axially extending openings in the other of the first and second connector modules.

22. The device of claim 21, wherein the first connector module is integrally formed with the first end plate, and the second connector module is integrally formed with the second end plate.

* * * * *